United States Patent [19]

Condon et al.

[11] Patent Number: 5,464,808

[45] Date of Patent: Nov. 7, 1995

[54] 1-[α-CYCLOPROPYL-α-(SUBSTITUTED OXY)-O-TOLYL]SULFAMOYL]-3-(4,6-DIMETHOXY-2-PYRIMIDINYL)UREA HERBICIDAL AGENTS

[75] Inventors: Michael E. Condon, Lawrenceville; Philip M. Harrington, Cranbury, both of N.J.

[73] Assignee: American Cyanamid Company, Wayne, N.J.

[21] Appl. No.: 174,506

[22] Filed: Dec. 28, 1993

[51] Int. Cl.$^6$ .................... C07D 239/69; C07D 239/52; C07D 239/42; A01N 43/54
[52] U.S. Cl. ............................. 504/214; 544/321
[58] Field of Search .............................. 544/321; 504/214

[56] References Cited

U.S. PATENT DOCUMENTS

| | | | |
|---|---|---|---|
| 4,666,508 | 5/1987 | Van Gemert | 544/211 |
| 4,741,762 | 5/1988 | Van Gemert | 544/211 |
| 5,009,699 | 4/1991 | Brady et al. | 544/321 |
| 5,129,941 | 7/1992 | Loher | 504/214 |

Primary Examiner—John M. Ford
Attorney, Agent, or Firm—Gregory M. Hill

[57] ABSTRACT

There are provided 1-{[α-cyclopropyl-α-(substituted oxy)-o-tolyl]sulfamoyl}-3-(4,6-dimethoxy-2-pyrimidinyl)urea compounds of formula I

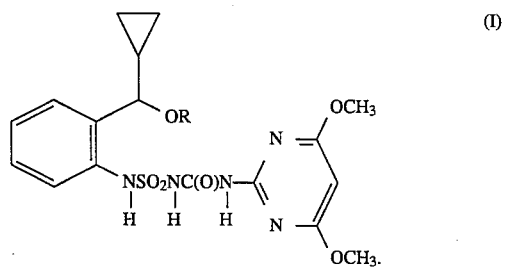

Further provided are compositions and methods comprising those compounds for the control of undesirable plant species.

25 Claims, No Drawings

1-[α-CYCLOPROPYL-α-(SUBSTITUTED OXY)-O-TOLYL]SULFAMOYL]-3-(4,6-DIMETHOXY-2-PYRIMIDINYL)UREA HERBICIDAL AGENTS

BACKGROUND OF THE INVENTION

Weeds cause tremendous global economic losses by reducing crop yields and lowering crop quality. In the United States alone, agronomic crops must compete with hundreds of weed species, including barnyardgrass, broadleaf weeds and sedges. Moreover, the application of some herbicides to control such undesirable plant species has caused some crop damage due to inadvertent exposure to those herbicides.

Therefore, research efforts continue to discover and develop more effective herbicidal agents for the selective control of weeds. Such agents are desirably effective even while growing in the presence of crops so that inadvertent uneven application will cause less crop damage, if not eliminating such damage altogether.

Sulfamoyl urea derivatives are described in U.S. Pat. Nos. 4,666,508 and 4,741,762. The sulfamoyl urea derivatives disclosed therein demonstrate herbicidal activity but do not provide a showing of selective weed control in the presence of crops.

U.S. Pat. No. 5,009,699 discloses a crop-selective, herbicidal sulfamoyl urea derivative. However, that compound is outside the scope of the present invention.

It is an object of the present invention to provide compounds which are highly effective for controlling undesirable plant species.

It is also an object of the present invention to provide a method for controlling undesirable plant species.

It is a further object of this invention to provide a method for the selective control of undesirable plant species growing in the presence of crops.

These and other objects of the present invention will become more apparent from the detailed description thereof set forth below.

SUMMARY OF THE INVENTION

The present invention describes 1-{[α-cyclopropyl-α-(substituted oxy)-o-tolyl]sulfamoyl}-3-(4,6-dimethoxy-2-pyrimidinyl)urea compounds which are useful as herbicidal agents.

The 1-{[α-cyclopropyl-α-(substituted oxy)-o-tolyl]sulfamoyl}-3-(4,6-dimethoxy-2-pyrimidinyl)urea compounds of the present invention have the following structural formula I:

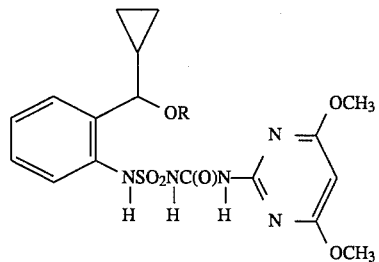

wherein
R is hydrogen, $C(O)R_1$, or $C_1$–$C_6$alkyl optionally interrupted by one O or S atom, or optionally substituted with one or more $C_1$–$C_4$alkoxy, halogen, hydroxy, oxo or $C_1$–$C_6$carbalkoxy groups;

$R_1$ is $C_1$–$C_6$alkyl, optionally substituted with one or more $C_1$–$C_4$alkoxy, halogen or hydroxy groups, phenyl optionally substituted with one or more $C_1$–$C_4$alkyl, $C_1$–$C_4$alkoxy, halogen or hydroxy groups, or $NR_2R_3$; and $R_2$ and $R_3$ are each independently hydrogen or $C_1$–$C_6$alkyl.

This invention also relates to compositions containing those compounds and methods for using those compounds and compositions in controlling undesirable plant species. The compounds of the present invention are especially useful for the selective control of a variety of undesirable plant species in the presence of cereal crops.

DETAILED DESCRIPTION OF THE INVENTION

Advantageously, the present invention provides a method for controlling undesirable plant species by applying to the foliage of said plants, or to the soil or water containing seeds or other propagating organs thereof, a herbicidally effective amount of a formula I compound.

The present invention also provides a method for the selective control of undesirable plant species in the presence of cereal crops, by applying to the foliage and stems of the crops and undesirable plant species growing in the presence thereof, or to the soil or water containing seeds or other propagating organs of the undesirable plant species in which the crops are growing, an amount of a formula I compound effective for the selective control of the undesirable plant species growing in the presence of the crops.

The present invention further provides a method for the control of undesirable plant species in transplanted rice by applying to the soil or water containing seeds or other propagating organs of said undesirable plant species, after the rice has been transplanted, a herbicidally effective amount of a formula I compound.

The 1-{[α-cyclopropyl-α-(substituted oxy)-o-tolyl]sulfamoyl}-3-(4,6-dimethoxy-2-pyrimidinyl)urea compounds of the present invention have the following structural formula I:

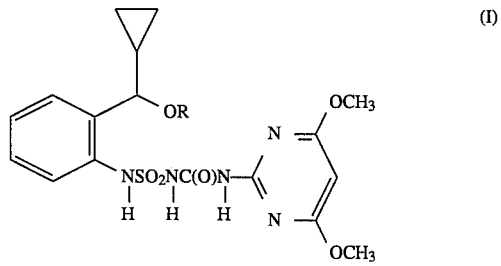

wherein R is as described hereinabove for formula I.

Preferred formula I compounds of the present invention are those wherein

R is hydrogen or $C(O)R_1$; and $R_1$ is $C_1$–$C_6$alkyl.

A most preferred formula I compound of the present invention which is a particularly effective herbicidal agent or for controlling undesirable plant species is 1-[(α-cyclopropyl-α-hydroxy-o-tolyl)sulfamoyl]-3-(4,6-dimethoxy-2-pyrimidinyl)urea.

In the formula I compounds described hereinabove the term halogen includes fluorine, chlorine, bromine and iodine.

Advantageously, it has been found that the formula I compounds of the present invention are especially useful for the selective control of barnyardgrass, broadleaf weeds and sedges in the presence of cereal crops.

Methods for preparing such useful compositions are disclosed herein. For example, 1-[(α-cyclopropyl-α-hydroxy-o-tolyl)-sulfamoyl]-3-(4,6-dimethoxy-2-pyrimidinyl)urea may be prepared by the reaction of 2-amino-4,6-dimethoxypyrimidine with chlorosulfonyl isocyanate in the presence of methylene chloride, followed by treatment of the thus prepared reaction mixture with o-amino-α-cyclopropyl-benzyl alcohol and triethylamine in the presence of methylene chloride, to form the desired compound.

Other compounds of formula I wherein R is C(O)R$_1$ may be prepared as shown below in Flow Diagram I.

FLOW DIAGRAM I

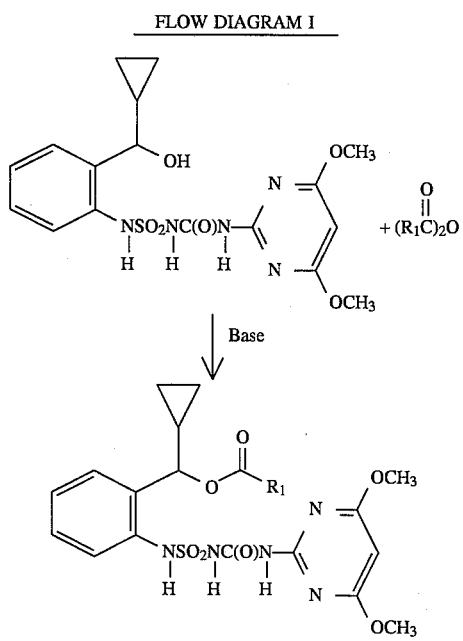

The formula I compounds of the present invention are effective herbicidal agents useful for the control of a wide variety of undesirable plant species. Those compounds are effective for controlling weeds native to both dry land and wetland areas. The compounds are also useful as aquatic herbicides and are effective in controlling the above-said undesirable plants when applied to the foliage thereof or to soil or water containing seeds or other propagating organs thereof, such as stolons, tubers or rhizomes, at rates of from about 0.016 to 4.0 kg/ha and preferably from about 0.125 to 1.0 kg/ha. Of course, higher rates may be used to equal effect, but use at such higher rates is deemed to be economically wasteful and environmentally undesirable.

Advantageously, it has been found that the compounds of the present invention, especially 1-[(α-cyclopropyl-α-hydroxy-o-tolyl)sulfamoyl]-3-(4,6-dimethoxy-2-pyrimidinyl)urea, are effective for controlling undesirable plant species including important weeds in transplanted rice culture such as barnyardgrass, broadleaf weeds and sedges. The compounds may be applied to the soil or water containing transplanted rice plants and seeds or other propagating organs of a variety of weed species at rates of from about 0,016 to 4.0 kg/ha.

The compounds of the present invention, especially 1-[(α-cyclopropyl-α-hydroxy-o-tolyl)-sulfamoyl]-3-(4,6-dimethoxy-2-pyrimidinyl)urea, are particularly suitable for the selective control of barnyardgrass, broadleaf weeds and sedges in the presence of cereal crops such as barley, wheat, oats, rye and rice. The compounds may be applied to the cereal crops and undesirable plant species, or to the soil or water containing seeds or other propagating organs of the undesirable plant species, at rates of from about 0.016 to 4.0 kg/ha.

While the compounds of this invention are effective for controlling undesirable plant species when employed alone, they may also be used in combination with other biological chemicals, including other herbicides.

The formula I compounds of this invention may be applied in the form of a solid or liquid herbicidal composition, comprising a herbicidally effective amount of the formula I compound dispersed or dissolved in an agronomically acceptable solid or liquid carrier. The formulations may be applied as preemergence or postemergence treatments.

Advantageously, the formula I compounds may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims. The terms NMR and MS designate nuclear magnetic resonance and mass spectroscopy, respectively.

EXAMPLE 1

Preparation of o-Amino-α-cyclopropylbenzyl alcohol

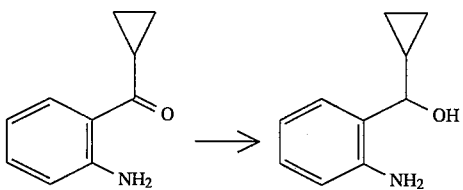

To a solution of o-aminophenyl cyclopropyl ketone (7.78 g, 48.3 mmol) in tetrahydrofuran at 0° C. is added 29 mL of a 1.0M lithium aluminum hydride solution in tetrahydrofuran. The reaction mixture is stirred at 0° C. for 2 hours, warmed to and stirred at room temperature for 16 hours, quenched with saturated ammonium chloride solution and extracted with ethyl acetate. The combined organic extracts are dried over anhydrous sodium sulfate and concentrated in vacuo to obtain a residue. Flash column chromatography of the residue using silica gel and 30% to 50% ethyl acetate in hexanes solutions gives the title product as a yellow solid (5.02 g, 64%, mp 76°–79° C.) which is identified by $^1$HNMR and MS spectral analyses.

EXAMPLE 2

Preparation of
1-[(α-cyclopropyl-α-hydroxy-o-tolyl)sulfamoyl]
-3-(4,6-dimethoxy-2-pyrimidinyl)urea

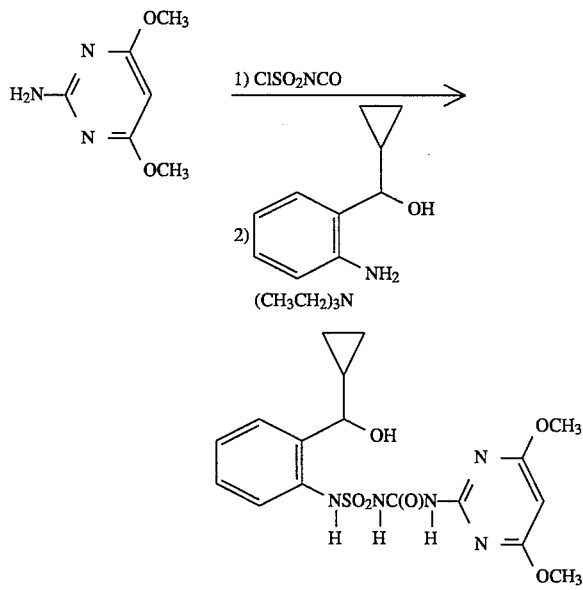

Chlorosulfonyl isocyanate (0.53 mL, 0.86 g, 6.1 mmol) is added to a solution of 2-amino-4,6-dimethoxypyrimidine (0.95 g, 6.1 mmol) in methylene chloride at 0° C. The resulting mixture is stirred for 30 minutes and a solution of o-amino-α-cyclopropylbenzyl alcohol (1.00 g, 6.1 mmol) and triethylamine (1.45 mL, 1.05 g, 10.4 mmol) in methylene chloride is slowly added to the mixture. The resulting solution is stirred at room temperature for hours, concentrated in vacuo and dissolved in methanol. The methanol solution is adjusted to about pH 1 with 10% hydrochloric acid and extracted with methylene chloride. The combined organic extracts are dried over anhydrous sodium sulfate and concentrated in vacuo to obtain a residue. Flash column chromatography of the residue using silica gel and 30% to 50% ethyl acetate in hexanes solutions gives the title product as a white solid (0.55 g, 21%, mp 66°–69° C.) which is identified by $^1$HNMR and MS spectral analyses.

EXAMPLE 3

Preparation of
1-{[o-(cyclopropylhydroxymethyl)phenyl]
sulfamoyl}-3-(4,6-dimethoxy-2-pyrimidinyl)urea
acetate (ester)

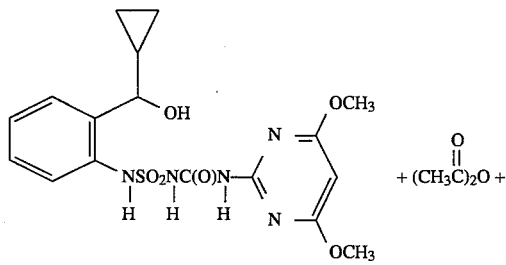

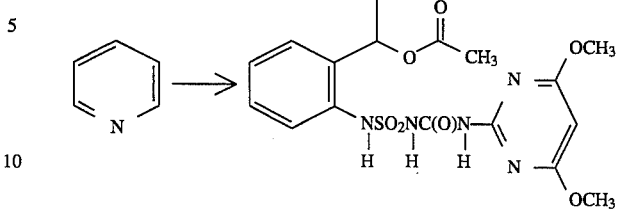

Acetic anhydride (0.18 mL, 0.19 g, 1.9 mmol) is added to a mixture of 1-[(α-cyclopropyl-α-hydroxy-o-tolyl)sulfamoyl]-3-(4,6-dimethoxy-2-pyrimidinyl)urea (0.40 g, 0.9 mmol) in pyridine. The reaction mixture is stirred at room temperature for 18 hours, treated with additional acetic anhydride (0.27 mL, 2.9 mmol), stirred for 5 hours, diluted with water and extracted with ether. The combined organic extracts are dried over anhydrous sodium sulfate and concentrated in vacuo to obtain a residue. Flash column chromatography of the residue using silica gel and 50% to 75% ethyl acetate in hexanes solutions gives the title product as a white powder (0.10 g, 23%, mp 156°–158° C.) which is identified by $^1$HNMR and MS spectral analyses.

EXAMPLE 4

Rice tolerance to post-transplant applications and preemergence weed control under flooded paddy conditions The tolerance of transplanted rice to post-transplanted herbicide applications is measured as follows: Two ten-day-old rice seedlings (CV. Tebonnet) are transplanted into silt loam soil in 32 oz plastic containers having a diameter of 10.5 cm and no drainage holes. After transplant, the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of 1.0, 0.5, 0.25, 0.125, 0.063 and 0.032 kg/ha of active ingredient. The treated containers are placed on greenhouse benches, watered such that the water level is maintained as stated above, and cared for according to normal greenhouse procedures. Three to four weeks after treatment the test is terminated and each container is examined and herbicidal effect rated according to the rating system set forth below. The data obtained are reported in Table I.

Preemergence herbicidal activity under flooded paddy conditions is determined as follows: plant seeds or propagating organs are planted in the top 0.5 cm of silt loam soil in 32 oz plastic containers with a diameter of 10.5 cm and no drainage holes. Water is added to these containers and maintained at 1.5 to 3 cm above the soil surface for the duration of the experiment. The test compounds are applied as an aqueous/acetone mixture 50/50 v/v pipetted directly into the flood water to give the equivalent of 1.0, 0.5, 0.25, 0.125, 0.063 and 0.032 kg/ha of active ingredient. The treated containers are placed on greenhouse benches and cared for according to normal greenhouse procedures. Three to four weeks after treatment the test is terminated and each container is examined and herbicidal effect rated according to the rating system set forth below. The data obtained are reported in Table I.

Plant species employed in this example are reported by header abbreviation, common name and scientific name.

| Header Abb. | Common Name | Scientific Name |
|---|---|---|
| \multicolumn{3}{c}{PLANT SPECIES EMPLOYED IN HERBICIDAL EVALUATIONS} | | |
| ECHCG | Barnyardgrass | ECHINOCHLOA CRUS-GALLI, (L)BEAU |
| CYPSE | Flatstage | CYPERUS SEROTINUS, ROTTB. |
| ELOKU | Eleocharis Kuroguwai | ELEOCHARIS KUROGUWAI |
| MOOVA | Monochoria | MONOCHORIA VAGINALIS, PRESL. |
| SAGPY | Arrowhead (pygmaea) | SAGITTARIA PYGMAEA, L. |
| ORYSP | Rice, Transplanted | ORYZA SATIVA-Transplanted |

Herbicide Rating Scale

Results of herbicide evaluation are expressed on a rating scale (0–9). The scale is based upon a visual observation of plant stand, vigor, malformation, size, chlorosis and overall plant appearance as compared with an untreated control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | | rimidinyl) urea is especially useful for the preemergence control of barnyardgrass, flatstage, monochoria and arrowhead in the presence of transplanted paddy rice.

EXAMPLE 5

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint containers. After planting, the containers are sprayed with the selected aqueous acetone solution containing test compound in sufficient quantity to provide the equivalent of about 0.125 to 0.50 kg per hectare of test compound per container. The treated containers are then placed on greenhouse benches, watered and cared for in accordance with conventional greenhouse procedures. From four to five weeks after treatment, the tests are terminated and each container is examined and rated according to the rating system provided in Example 4.

The data obtained are reported in Table II below. Where more than one test is involved for a given compound, the data are averaged.

Plant species employed in these evaluations are reported by header abbreviation, common name and scientific name.

Compounds employed in this evaluation are given a compound number and identified by name. Data in Table II are reported by compound number.

TABLE I

PADDY CONDITIONS - POST-TRANSPLANT RICE PREEMERGENCE WEEDS

| Compound | Rate kg/ha | ECHCG | CYPSE | ELOKU | MOOVA | SAGPY | ORYSP |
|---|---|---|---|---|---|---|---|
| 1-[(α-Cyclopropyl-α-hydroxy-o-tolyl)sulfamoyl]-3-(4,6-dimethoxy-2-pyrimidinyl)urea | 1.000 | 9.0 | 9.0 | 9.0 | 9.0 | 9.0 | 3.0 |
| | 0.500 | 9.0 | 9.0 | 9.0 | 9.0 | 9.0 | 3.0 |
| | 0.250 | 9.0 | 9.0 | 9.0 | 9.0 | 9.0 | 2.0 |
| | 0.125 | 9.0 | 9.0 | 7.0 | 9.0 | 8.0 | 1.0 |
| | 0.063 | 8.0 | 9.0 | 5.0 | 9.0 | 8.0 | 1.0 |
| | 0.032 | 6.0 | 8.0 | 4.0 | 9.0 | 8.0 | 0.0 |

As can be seen from the data in Table I, 1-[(α -cyclopropyl-α-hydroxy-o-tolyl)sulfamoyl]-3-(4,6 -dimethoxy-2-py-

PLANT SPECIES EMPLOYED IN HERBICIDAL EVALUATIONS

| Header Abb. | Common Name | Scientific Name |
|---|---|---|
| ABUTH | Velvetleaf | ABUTILON THEOPHRASTI, MEDIC. |
| AMBEL | Ragweed, Common | AMBROSIA ARTEMISIIFOLIA, L. |
| CAGSE | Bindweed, Hedge | CALYSTEGIA SEPIUM |
| CAPBP | Shepherdspurse | CAPSELLA BURSA-PASTORIS (L)MEDI |

-continued
PLANT SPECIES EMPLOYED IN HERBICIDAL EVALUATIONS

| Header Abb. | Common Name | Scientific Name |
|---|---|---|
| CHEAL | Lambsquarters, Common | *CHENOPODIUM ALBUM*, L. |
| IPOSS | Morningglory, Spp. | IPOMOEA SPP. |
| SINAR | Mustard, Wild | *BRASSICA KABER*, (DC)L.C.WHEELR |
| STEME | Chickweed, Common | *STELLARIA MEDIA*, L., CYRILLO |
| ECHCG | Barnyardgrass | *ECHINOCHLOA CRUS-GALLI*, (L)BEAU |
| CYPRO | Nutsedge, Purple | *CYPERUS ROTUNDUS*, L. |
| HORVSB | Barley, Spring, Bonanza | *HORDEUM VULGARE* CV. BONANZA |
| TRZASK | Wheat, Spring, Katep | *TRITICUM AESTIVUM*, KATEPWA |
| GALAP | Galium | *GALIUM APARINE* |
| KCHSC | Kochia | *KOCHIA SCOPARIA*, (L)ROTH |
| MATSS | Mayweed Sp. | MATRICARIA SPP. |
| POLCO | Buckwheat, Wild | *POLYGONUM CONVOLVULUS*, L. |
| RUMCR | Dock, Curly | *RUMEX CRISPUS*, L. |
| SOLNI | Nightshade, Black | *SOLANUM NIGRUM*, L. |
| THLAR | Field Pennycress | *THLASPI ARVENSE* L. |
| HORVWA | Barley, Winter, Marinka | *HORDEUM VULGARE*, CV. MARINKA |
| TRZASO | Wheat, Spring, Olaf | *TRITICUM AESTIVUM*, CV OLAF |

COMPOUNDS EVALUATED AS HERBICIDAL AGENTS

| Compound No. | |
|---|---|
| 1 | 1-[($\alpha$-Cyclopropyl-$\alpha$-hydroxy-o-tolyl)sulfamoyl]-3-(4,6-dimethoxy-2-pyrimidinyl)urea |
| 2 | 1-{[o-(Cyclopropylhydroxymethyl)phenyl]-sulfamoyl}-3-(4,6-dimethoxy-2-pyrimidinyl)urea acetate (ester) |

TABLE II
Preemergence Herbicidal Evaluations of Test Compounds

| Cpd No. | Rate (kg/ha) | ABUTH | AMBEL | CAGSE | CAPBP | CHEAL | IPOSS |
|---|---|---|---|---|---|---|---|
| 1 | 0.500 | 6.7 | 8.3 | 8.0 | 9.0 | 9.0 | 7.0 |
|   | 0.250 | 5.0 | 8.0 | 8.0 | 9.0 | 9.0 | 7.0 |
|   | 0.125 | 3.0 | 6.7 | 4.7 | 9.0 | 8.0 | 5.0 |
| 2 | 0.500 | 6.0 | 8.0 | 9.0 | — | 9.0 | 4.0 |
|   | 0.250 | 2.0 | 7.0 | 9.0 | — | 8.0 | 1.0 |
|   | 0.125 | 0.0 | 3.0 | 2.0 | — | — | 0.0 |

| Cpd No. | Rate (kg/ha) | SINAR | STEME | ECHCG | CYPRO | HORVSB | TRZASK |
|---|---|---|---|---|---|---|---|
| 1 | 0.500 | 9.0 | 8.0 | 8.0 | 8.0 | 0.0 | 1.3 |
|   | 0.250 | 9.0 | 9.0 | 7.3 | 7.3 | 0.0 | 0.7 |
|   | 0.125 | 8.8 | 9.0 | 5.7 | 6.3 | 0.0 | 0.3 |
| 2 | 0.500 | 9.0 | — | 4.0 | 9.0 | 0.0 | 1.0 |
|   | 0.250 | 9.0 | — | 0.0 | 7.0 | 0.0 | 0.0 |
|   | 0.125 | 8.0 | — | 0.0 | 4.0 | 0.0 | 0.0 |

EXAMPLE 6

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.125 kg to 0.500 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 4.

The data obtained for 1-[(α-cyclopropyl-α-hydroxy-o-tolyl)sulfamoyl]-3-(4,6-dimethoxy-2-pyrimidinyl)urea and 1-{[o-(cyclopropylhydroxymethyl)phenyl]sulfamoyl}-3-(4,6-dimethoxy-2-pyrimidinyl)urea acetate (ester) are reported in Tables III and IV, respectively.

TABLE III

Postemergence Herbicidal Evaluation of 1-[(α-Cyclopropyl-α-hydroxy-o-tolyl)-sulfamoyl]-3-(4,6-dimethoxy-2-pyrimidinyl)urea

| Rate (kg/ha) | CAPBP | GALAP | KCHSC | MATSS | POLCO | RUMCR |
|---|---|---|---|---|---|---|
| 0.500 | 9.0 | 9.0 | 3.0 | 9.0 | 9.0 | 9.0 |
| 0.250 | 9.0 | 9.0 | 0.0 | 9.0 | 9.0 | 8.0 |
| 0.125 | 9.0 | — | 0.0 | 8.0 | 8.0 | 6.0 |

| Rate (kg/ha) | SINAR | SOLNI | STEME | THLAR | HORVWA | TRZASO |
|---|---|---|---|---|---|---|
| 0.500 | 9.0 | 9.0 | 4.0 | 9.0 | 0.0 | 0.0 |
| 0.250 | 9.0 | 8.0 | 0.0 | 9.0 | 0.0 | 0.0 |
| 0.125 | 8.0 | 7.0 | 0.0 | 7.0 | 0.0 | 0.0 |

TABLE IV

Postemergence Herbicidal Evaluation of 1-{[o-(Cyclopropylhydroxymethyl)phenyl]-sulfamoyl}-3-(4,6-dimethoxy-2-pyrimidinyl)urea acetate (ester)

| Rate (kg/ha) | ABUTH | AMBEL | CAGSE | CHEAL | IPOSS | SINAR | ECHCG | CYPRO | HORVSB | TRZASK |
|---|---|---|---|---|---|---|---|---|---|---|
| 0.250 | 2.0 | 0.0 | 9.0 | 3.0 | 4.0 | 9.0 | 2.0 | 4.0 | 0.0 | 0.0 |
| 0.125 | 0.0 | 0.0 | 4.0 | 3.0 | 4.0 | 9.0 | 0.0 | 2.0 | 0.0 | 0.0 |

What is claimed is:

1. A compound having the structural formula

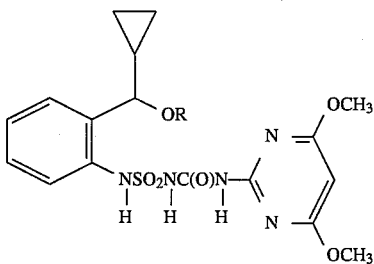

wherein

R is hydrogen, C(O)R$_1$, or C$_1$–C$_6$alkyl optionally interrupted by one O or S atom, or optionally substituted with one or more C$_1$–C$_4$alkoxy, halogen, hydroxy, oxo or C$_1$–C$_6$carbalkoxy groups;

R$_1$ is C$_1$–C$_6$alkyl, optionally substituted with one or more C$_1$–C$_4$alkoxy, halogen or hydroxy groups, phenyl optionally substituted with one or more C$_1$–C$_4$alkyl, C$_1$–C$_4$alkoxy, halogen or hydroxy groups, or NR$_2$R$_3$; and R$_2$ and R$_3$ are each independently hydrogen or C$_1$–C$_6$alkyl.

2. The compound according to claim 1 wherein
R is hydrogen or C(O)R$_1$; and
R$_1$ is C$_1$–C$_6$alkyl.

3. The compound according to claim 2, 1-[(α-cyclopropyl-α-hydroxy-o-tolyl)sulfamoyl]-3-(4,6-dimethoxy-2-pyrimidinyl)urea.

4. The compound according to claim 2, 1-{[o-(cyclopropylhydroxymethyl)phenyl]sulfamoyl}-3-(4,6-dimethoxy-2-pyrimidinyl)urea acetate (ester).

5. A method for controlling undesirable plant species which comprises applying to the foliage of said plants, or to the soil or water containing seeds or other propagating organs thereof, a herbicidally effective amount of a compound having the structural formula

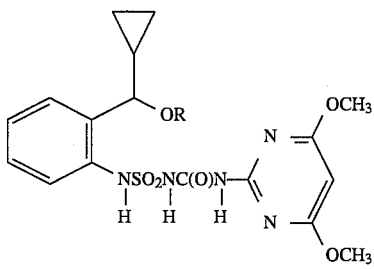

wherein R is described in claim 1.

6. The method according to claim 5 wherein
R is hydrogen or C(O)R$_1$; and
R$_1$ is C$_1$–C$_6$alkyl.

7. The method according to claim 6 wherein the compound is 1-[(α-cyclopropyl-α-hydroxy-o-tolyl)sulfamoyl]-3-(4,6-dimethoxy-2-pyrimidinyl)urea.

8. The method according to claim 6 wherein the compound is 1-{[o-(cyclopropylhydroxymethyl)phenyl]sulfamoyl} -3-(4,6-dimethoxy-2-pyrimidinyl)urea acetate (ester).

9. The method according to claim 5 which comprises applying said compound to the foliage of said plants or to the soil or water containing seeds or other propagating organs thereof at a rate of about 0.016 kg/ha to 4.0 kg/ha.

10. The method according to claim 5 wherein said method is effective for the selective control of undesirable plant species in the presence of cereal crops.

11. The method according to claim 10 wherein

R is hydrogen or $C(O)R_1$; and $R_1$ is $C_1-C_6$alkyl.

12. The method according to claim 11 wherein the compound is 1-[(α-cyclopropyl-α-hydroxy-o-tolyl)sulfamoyl]-3-(4,6-dimethoxy-2-pyrimidinyl)urea.

13. The method according to claim 11 wherein the compound is 1-{[o-(cyclopropylhydroxymethyl)phenyl]sulfamoyl}-3-(4,6-dimethoxy-2-pyrimidinyl)urea acetate (ester).

14. The method according to claim 10 wherein the undesirable plant species are selected from the group consisting of barnyardgrass, broadleaf weeds and sedges, and the cereal crops are selected from the group consisting of barley, wheat, oats, rye and rice.

15. The method according to claim 10 wherein the compound is applied to the crops and undesirable plant species or to the soil or water containing seeds or other propagating organs of the undesirable plant species at a rate of about 0.016 kg/ha to 4.0 kg/ha.

16. A method for the control of undesirable plant species in transplanted rice which comprises applying to the soil or water containing seeds or other propagating organs of said undesirable plant species, after the rice has been transplanted, a herbicidally effective amount of a compound having the structural formula

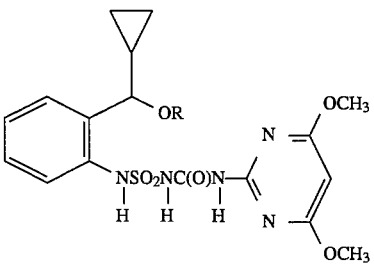

wherein R is described in claim 1.

17. The method according to claim 16 wherein

R is hydrogen or $C(O)R_1$; and $R_1$ is $C_1-C_6$alkyl.

18. The method according to claim 17 wherein the compound is 1-[(α-cyclopropyl-α-hydroxy-o-tolyl)sulfamoyl]-3-(4,6-dimethoxy-2-pyrimidinyl)urea.

19. The method according to claim 17 wherein the compound is 1-{[o-(cyclopropylhydroxymethyl)phenyl]sulfamoyl}-3-(4,6-dimethoxy-2-pyrimidinyl)urea acetate (ester).

20. The method according to claim 16 wherein the undesirable plant species are selected from the group consisting of barnyardgrass, broadleaf weeds and sedges.

21. The method according to claim 16 wherein the compound is applied to the soil or water containing seeds or other propagating organs of the undesirable plant species at a rate of about 0.016 kg/ha to 4.0 kg/ha.

22. A herbicidal composition which comprises an agronomically acceptable solid or liquid carrier and a herbicidally effective amount of a compound having the structural formula

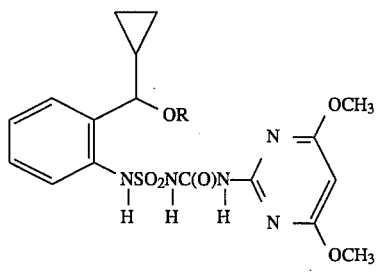

wherein R is described in claim 1.

23. The method according to claim 22 wherein

R is hydrogen or $C(O)R_1$; and $R_1$ is $C_1-C_6$alkyl.

24. The composition according to claim 23 wherein the compound is 1-[(α-cyclopropyl-α-hydroxy-o-tolyl)sulfamoyl]-3-(4,6-dimethoxy-2-pyrimidinyl)urea.

25. The composition according to claim 23 wherein the compound is 1-{[o-(cyclopropylhydroxymethyl)phenyl]sulfamoyl}-3-(4,6-dimethoxy-2-pyrimidinyl)urea acetate (ester).

* * * * *